United States Patent
Shindo

(10) Patent No.: US 9,900,971 B2
(45) Date of Patent: Feb. 20, 2018

(54) X-RAY CT APPARATUS, X-RAY HIGH-VOLTAGE DEVICE, AND X-RAY SCANNING DEVICE

(71) Applicant: HITACHI, LTD., Tokyo (JP)

(72) Inventor: Shotaro Shindo, Tokyo (JP)

(73) Assignee: HITACHI, LTD., Tokyo (JP)

( * ) Notice: Subject to any disclaimer, the term of this patent is extended or adjusted under 35 U.S.C. 154(b) by 241 days.

(21) Appl. No.: 14/903,198

(22) PCT Filed: Jul. 24, 2014

(86) PCT No.: PCT/JP2014/069504
§ 371 (c)(1),
(2) Date: Jan. 6, 2016

(87) PCT Pub. No.: WO2015/016117
PCT Pub. Date: Feb. 5, 2015

(65) Prior Publication Data
US 2016/0143120 A1    May 19, 2016

(30) Foreign Application Priority Data
Jul. 31, 2013   (JP) .................... 2013-159577

(51) Int. Cl.
*A61B 6/00*       (2006.01)
*H05G 1/66*       (2006.01)
(Continued)

(52) U.S. Cl.
CPC ............... *H05G 1/66* (2013.01); *A61B 6/032* (2013.01); *A61B 6/4021* (2013.01); *A61B 6/545* (2013.01); *H05G 1/56* (2013.01)

(58) Field of Classification Search
CPC ....... A61B 6/032; A61B 6/4021; A61B 6/545; H05G 1/56; H05G 1/66
See application file for complete search history.

(56) References Cited

U.S. PATENT DOCUMENTS

| | | |
|---|---|---|
| 6,088,425 A | 7/2000 | Ono |
| 2001/0012329 A1 | 8/2001 | Sato |
| 2004/0264643 A1 | 12/2004 | Chretien |

FOREIGN PATENT DOCUMENTS

| | | |
|---|---|---|
| JP | 59-217995 | 12/1984 |
| JP | 10-335092 | 12/1998 |

(Continued)

OTHER PUBLICATIONS

English translation dated Sep. 30, 2016 Chinese official action in corresponding Chinese Patent Application No. 201480039529.2.
International Search Report in PCT/JP2014/069504.

*Primary Examiner* — Dani Fox
(74) *Attorney, Agent, or Firm* — Cooper & Dunham LLP

(57) ABSTRACT

In order to provide an X-ray CT apparatus which reduces a waiting time period until irradiation with X-rays is permitted with a simple configuration without detecting a rotation speed of an anode, a controller (23) selects a rating anode rotation speed among a plurality of types thereof depending on an X-ray irradiation condition, and supplies driving power for realizing the selected rating anode rotation speed to a stator coil (81) from a starter circuit (10). The controller (23) obtains time required to reach an irradiation possible rotation speed which is lower than the rating anode rotation speed and is required to apply X-rays in an X-ray irradiation condition. If arrival time has elapsed, irradiation with X-rays is permitted. Consequently, it is possible to reduce a waiting time period in which an operator waits for an anode rotation speed to rise.

11 Claims, 9 Drawing Sheets

(51) Int. Cl.
*H05G 1/56* (2006.01)
*A61B 6/03* (2006.01)

(56) References Cited

FOREIGN PATENT DOCUMENTS

| | | |
|---|---|---|
| JP | 2000-286092 | 10/2000 |
| JP | 2000-286093 | 10/2000 |
| JP | 2001-176693 | 6/2001 |
| JP | 2001-231775 | 8/2001 |
| JP | 2002-93596 | 3/2002 |
| JP | 2004-349254 | 12/2004 |
| JP | 2007-179817 | 7/2007 |
| JP | 2013-182764 | 9/2013 |

X-RAY CT APPARATUS, X-RAY HIGH-VOLTAGE DEVICE, AND X-RAY SCANNING DEVICE

TECHNICAL FIELD

The present invention relates to an X-ray CT apparatus provided with a starter device which rotates a rotary anode of an X-ray tube.

BACKGROUND ART

In an X-ray CT apparatus, a rotary anode type X-ray tube is used in order to minimize a thermal influence on an X-ray tube anode due to irradiation with X-rays. The rotary anode type X-ray tube is configured to include a stator coil disposed outside the tube, and a rotary anode disposed inside the tube. The stator coil is connected to a starter circuit. The starter circuit supplies a three-phase AC voltage or a voltage shifted by 90 degrees from a phase thereof, to the stator coil so as to generate a rotating magnetic field, thereby rotating the anode inside the tube. When the voltage starts to be supplied to the stator coil from the starter circuit, a rotation speed of the anode does not reach a predetermined rotation speed, and thus X-rays are applied after a predefined waiting time period elapses. The waiting time period is a time period required for the rotation speed of the anode to be increased to the predetermined rotation speed or higher, and is a fixed time period obtained in advance. Consequently, electron beams are prevented from being applied to a cathode from the anode before the predetermined rotation speed is reached.

On the other hand, PTL 1 discloses an X-ray apparatus which performs control of a rotation speed of an anode as follows. If an operator selects an X-ray tube device and inputs scanning conditions thereto, and a starter device obtains a model of the X-ray tube device and reads a rating corresponding to the model of the X-ray tube device from means for storing a relationship between a rotation speed and a rating of the rotary anode for each model of an X-ray tube device. Next, a retention rotation speed during scanning of the rotary anode of the X-ray tube device is calculated on the basis of the set scanning condition, and a rotation speed of the rotary anode of the X-ray tube device is increased to the calculated retention rotation speed during scanning and is then maintained. The starter device is provided with a rotation speed detector, and completion of a scanning preparation operation is displayed if a detected rotation speed is increased to the retention rotation speed during scanning. Consequently, since a rotation speed is not required to be increased to a high rotation speed in the same way and can thus be increased to the retention rotation speed during scanning corresponding to the scanning condition, it is possible to reduce an activation time.

CITATION LIST

Patent Literature

[PTL 1] JP-A-2000-286092

SUMMARY OF INVENTION

Technical Problem

However, in the method disclosed in PTL 1, since a rotation speed of the anode (retention rotation speed during scanning) is changed whenever a scanning condition is changed, control of a rotation speed of the anode is complex. For example, it is necessary to provide a detector which detects a rotation speed of the anode in real time inside the apparatus, and thus an apparatus configuration is complex. In addition, it is necessary to determine whether or not a detected rotation speed reaches the retention rotation speed during scanning, and thus a control circuit is also complex. Further, if this technique is to be applied to an X-ray CT apparatus, a detector detecting an anode rotation speed is required to be provided in a gantry, but it is hard for the detector to avoid an influence of vibration caused by rotation of the gantry and to detect an anode rotation speed with high accuracy.

In addition, in the technique disclosed in PTL 1, since an anode rotation speed is changed whenever a scanning condition is changed, in a case where X-rays are continuously applied while changing scanning conditions from a low rotation speed to a high rotation speed, a waiting time period for increasing a rotation speed by a difference between the rotation speeds is necessary. Conversely, in a case where an anode rotation speed is changed from a high rotation speed to a low rotation speed, thermal loss occurs in the stator coil, the starter circuit, or the like.

An object of the present invention is to provide an X-ray CT apparatus which reduces a waiting time period until irradiation with X-rays is permitted with a simple configuration without detecting a rotation speed of an anode.

Solution to Problem

In order to achieve the above-described object, in the present invention, a rating anode rotation speed is selected among a plurality of types thereof depending on an X-ray irradiation condition. A controller obtains time (arrival time) to reach an anode rotation speed (irradiation possible rotation speed) which is lower than the rating anode rotation speed and allows X-rays to be applied in an input X-ray irradiation condition. If the arrival time has elapsed, information indicating that irradiation with X-rays is possible is output.

Advantageous Effects of Invention

According to the present invention, it is possible to provide an X-ray CT apparatus which reduces a waiting time period until irradiation with X-rays is permitted with a simple configuration without detecting a rotation speed of an anode.

DESCRIPTION OF EMBODIMENTS

Figure 1:
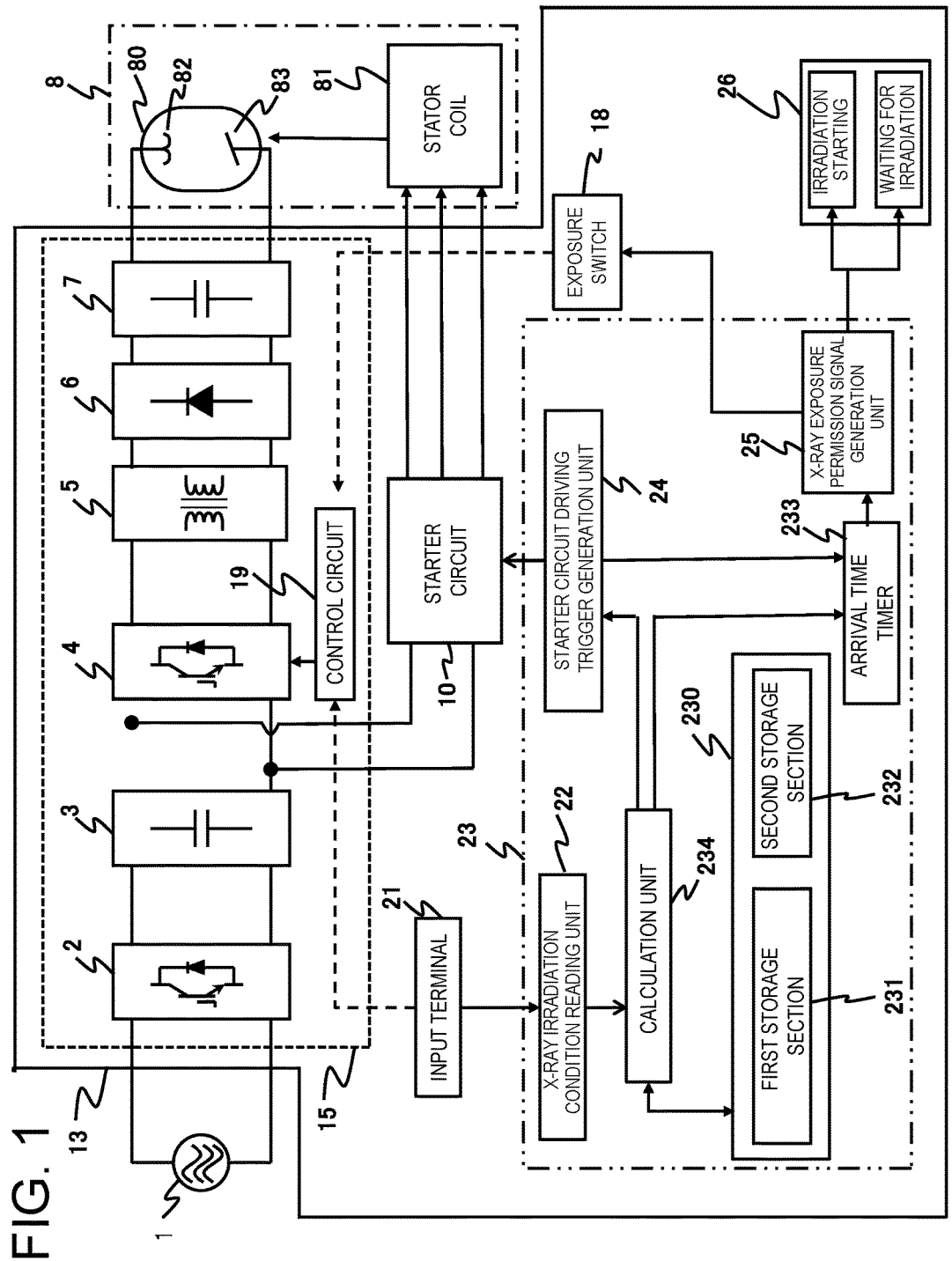
FIG. 1 is a block diagram illustrating a configuration of an X-ray high-voltage device 12 and the rotary anode type X-ray tube device 8 of an X-ray CT apparatus of Embodiment 1 of the present invention.

According to the present invention, there is provided an X-ray CT apparatus including an input unit that receives an X-ray irradiation condition for a mounted rotary anode type X-ray tube device; a starter circuit that supplies driving power for rotating an anode to the rotary anode type X-ray tube device; and a controller, in which the controller selects one of predefined two or more types of rating anode rotation speeds depending on the X-ray irradiation condition received by the input unit, and instructs the starter circuit to supply driving power for realizing the selected rating anode rotation speed, and obtains an arrival time required for a rotation speed of the anode to reach an irradiation possible rotation speed which is lower than the rating anode rotation speed and is required to apply X-rays in the X-ray irradiation condition received by the input unit, and outputs information indicating that irradiation with X-rays is possible to a display unit after the arrival time has elapsed from starting the supply of the driving power by the starter circuit.

The controller includes a storage unit that stores a relationship between various X-ray irradiation conditions and the arrival time, and reads the arrival time corresponding to the X-ray irradiation condition received by the input unit from the storage unit.

The controller obtains an irradiation possible rotation speed required to apply X-rays in the X-ray irradiation condition received by the input unit, and obtains the arrival time on the basis of the irradiation possible rotation speed.

The controller includes a first storage section that stores a relationship between various X-ray irradiation conditions and the irradiation possible rotation speed, and a second storage section that stores a relationship between the irradiation possible rotation speed and the arrival time, reads the irradiation possible rotation speed corresponding to the X-ray irradiation condition received by the input unit from the first storage section, and reads the arrival time corresponding to the read irradiation possible rotation speed from the second storage section.

The X-ray CT apparatus further includes a focal position control portion that changes a focal position on the anode of an electron beam emitted from a cathode of the rotary anode type X-ray tube device, and the X-ray irradiation condition received by the input unit includes an amplitude of the focal position.

The controller includes a first storage section that stores a relationship between other X-ray irradiation conditions excluding an amplitude of a focal position and the irradiation possible rotation speed for each amplitude of the focal position included in the X-ray irradiation conditions, and a second storage section that stores a relationship between the irradiation possible rotation speed and the arrival time, reads the irradiation possible rotation speed corresponding to the X-ray irradiation conditions including the amplitude received by the input unit from the first storage section, and reads the arrival time corresponding to the read irradiation possible rotation speed from the second storage section.

The X-ray CT apparatus further includes a heat unit calculation unit that calculates a heat unit applied to the anode of the rotary anode type X-ray tube device, and heat units accumulated in the anode over an elapsed time period, and the controller obtains the arrival time required for a rotation speed of the anode to reach the irradiation possible rotation speed on the basis of the heat unit obtained by the heat unit calculation unit.

In addition, the controller includes a first storage section that stores a relationship between an X-ray irradiation condition and the irradiation possible rotation speed, and a second storage section that stores a relationship between the irradiation possible rotation speed and the arrival time for each heat unit within a predetermined range, reads the irradiation possible rotation speed corresponding to the X-ray irradiation condition received by the input unit from the first storage section, and reads the arrival time corresponding to the read irradiation possible rotation speed from the second storage section on the basis of the heat unit obtained by the heat unit calculation unit.

The X-ray CT apparatus further includes a rotation portion that mounts the rotary anode type X-ray tube device thereon; and a rotation driving portion that rotates the rotation portion around an object.

According to the present invention, there is provided an X-ray high-voltage device including an input unit that receives an X-ray irradiation condition for a rotary anode type X-ray tube device; a starter circuit that supplies driving power for rotating an anode to the rotary anode type X-ray tube device; and a controller, in which the controller selects one of predefined two or more types of rating anode rotation speeds depending on the X-ray irradiation condition received by the input unit, and instructs the starter circuit to supply driving power for realizing the selected rating anode rotation speed, and obtains an arrival time required for a rotation speed of the anode to reach an irradiation possible rotation speed which is lower than the rating anode rotation speed and is required to apply X-rays in the X-ray irradiation condition received by the input unit, and outputs information indicating that irradiation with X-rays is possible to a display unit after the arrival time has elapsed from starting the supply of the driving power by the starter circuit.

According to the present invention, there is provided an X-ray scanning device including an input unit that receives an X-ray irradiation condition for a mounted rotary anode type X-ray tube device; a starter circuit that supplies driving power for rotating an anode to the rotary anode type X-ray tube device; and a controller, in which the controller selects one of predefined two or more types of rating anode rotation speeds depending on the X-ray irradiation condition received by the input unit, and instructs the starter circuit to supply driving power for realizing the selected rating anode rotation speed, and obtains an arrival time required for a rotation speed of the anode to reach an irradiation possible rotation speed which is lower than the rating anode rotation speed and is required to apply X-rays in the X-ray irradiation condition received by the input unit, and outputs information indicating that irradiation with X-rays is possible to a display unit after the arrival time has elapsed from starting the supply of the driving power by the starter circuit.

Hereinafter, embodiments of the present invention will be described in detail with reference to the drawings.

(Embodiment 1)

Hereinafter, a description will be made of an X-ray CT apparatus of Embodiment 1 of the present invention with reference to FIGS. 1 to 5.

The X-ray CT apparatus of Embodiment 1 includes, as illustrated in FIG. 1, an input unit (input terminal) 21 which receives an X-ray irradiation condition for a rotary anode type X-ray tube device 8 from an operator; a starter circuit 10 which supplies driving power for rotating an anode 83 to the rotary anode type X-ray tube device 8; and a controller 23. The controller 23 selects one of predefined two or more types of rating anode rotation speeds depending on an X-ray irradiation condition received by the input unit 21, and instructs the starter circuit 10 to supply driving power for realizing the selected rating anode rotation speed. In addition, the controller 23 obtains time (arrival time) for a rotation speed of the anode 83 to reach an irradiation possible rotation speed which is lower than the rating anode rotation speed and is required to apply X-rays in the X-ray irradiation condition received by the input unit 21. Further, if the arrival time has elapsed from starting the supply of the driving power by the starter circuit 10, information indicating that X-rays can be applied is displayed on a display unit 26.

As mentioned above, the controller 23 of the present invention selects a rating anode rotation speed among a plurality of types thereof depending on an X-ray irradiation condition, and supplies driving power for realizing the selected rating anode rotation speed. On the other hand, the controller 23 obtains arrival time to reach an irradiation possible rotation speed which is lower than the rating anode rotation speed and is required to apply X-rays in the X-ray irradiation condition. In addition, if the arrival time to reach the irradiation possible rotation speed has elapsed before reaching the rating anode rotation speed, irradiation with X-rays is permitted, and thus the operator's waiting time period can be reduced since the irradiation with X-rays can be started within a range in which a heat unit does not exceed a threshold value and in an anode rotation speed lower than the rating anode rotation speed depending on the X-ray irradiation condition.

In addition, since a rating anode rotation speed is selected among a plurality of types thereof in the same manner as in a general CT apparatus, a rating anode rotation speed is not required to be changed whenever an X-ray irradiation condition is slightly changed, and a configuration of the starter circuit can be simplified. Further, it is not necessary to detect an actual anode rotation speed since determination whether or not irradiation with X-rays can be performed is made by using arrival time. As mentioned above, according to the present invention, it is possible to reduce the operator's waiting time period by using the apparatus with a simple configuration.

The controller 23 may be configured to include a storage unit 230 which stores a relationship between various X-ray irradiation conditions and the above-described arrival times, and to read an arrival time corresponding to an X-ray irradiation condition received by the input unit 21 from the storage unit 230.

In addition, the controller 23 may be configured to obtain an irradiation possible rotation speed required to apply X-rays in an X-ray irradiation condition received by the input unit 21 and to obtain an arrival time on the basis of the irradiation possible rotation speed. In this case, the controller 23 is configured to include, for example, a first storage section 231 which stores a relationship between various X-ray irradiation conditions and irradiation possible rotation speeds, and a second storage section 232 which stores a relationship between irradiation possible rotation speeds and arrival times, to read an irradiation possible rotation speed corresponding to an X-ray irradiation condition received by the input unit 21 from the first storage section 231, and to read an arrival time corresponding to the read irradiation possible rotation speed from the second storage section 232.

Hereinafter, the X-ray CT apparatus of Embodiment 1 will be described in more detail.

As illustrated in FIG. 1, the X-ray CT apparatus includes the rotary anode type X-ray tube device 8; an X-ray high-voltage device 13 which supplies a tube current and a tube voltage to the rotary anode type X-ray tube device 8; an X-ray detector (not illustrated); and an image reconfiguring portion which reconfigures a tomographic image or the like of an object on the basis of an output signal from the X-ray detector. The rotary anode type X-ray tube device 8 and the X-ray detector are mounted on a rotation plate (not illustrated), irradiate an object with X-rays while being rotated around the object, and detect X-rays having transmitted through the object.

The rotary anode type X-ray tube device 8 has a structure in which a cathode 82 and the anode 83 are sealed in a tube 80. A stator coil 81 which generates a magnetic field for rotating a rotor connected to the anode 83 is provided outside the tube 80. The stator coil 81 is connected to the starter circuit 10. The starter circuit 10 supplies a driving current to the stator coil 81.

The X-ray high-voltage device 13 includes the starter circuit 10, a high voltage generation unit 15, the input terminal (input unit) 21, the controller 23, and the display unit 26.

Figure 2:
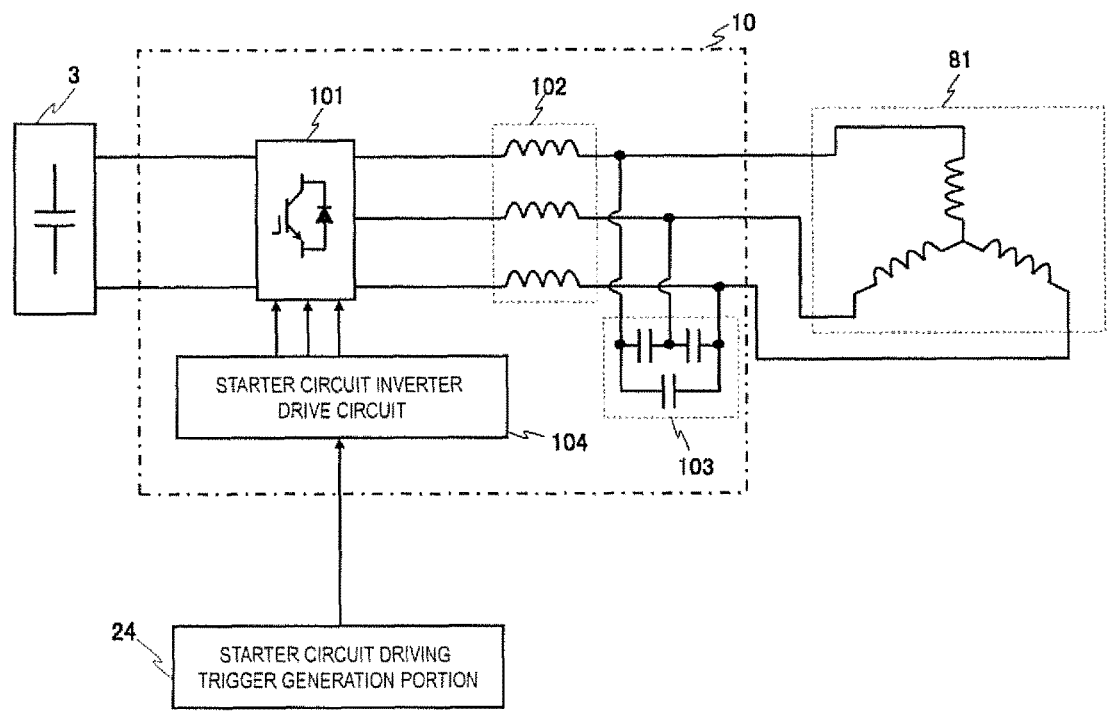
FIG. 2 is a block diagram illustrating a configuration of a starter circuit 10 of Embodiment 1.

FIG. 2 illustrates a configuration of the starter circuit. The starter circuit is configured to include a starter circuit inverter 101, an output filter inductor 102, an output filter capacitor 103, and a starter circuit inverter drive circuit 104. The starter circuit inverter drive circuit 104 starts an operation of the starter circuit inverter 101 when receiving a starter circuit driving start signal output from a starter circuit driving trigger generation unit 24 of the controller 23. The starter circuit inverter 101 converts a part of an output voltage from a DC bypass capacitor 3 into an AC voltage signal, and supplies the AC voltage signal to the stator coil 81 of the anode rotation type X-ray tube device 8 via the output filter inductor 102 and the output filter capacitor 103. The starter circuit inverter drive circuit 104 controls turning-on and turning-off timings of a switching circuit of the starter circuit inverter 101 so as to generate either a low rotation speed driving current (a frequency of 60 Hz, a voltage of 180 Vrms, and a current of 14 Arms) or a high rotation speed driving current (a frequency of 105 Hz, a voltage of 180 Vrms, and a current of 7 Arms) which is then supplied to the stator coil 81. Consequently, the anode 83 can be rotated at either one of two types of rating anode rotation speeds (a low rotation speed: 3600 rpm=60 Hz, and a high rotation speed: 6300 rpm=105 Hz).

The high voltage generation unit 15 is configured to include an AC-DC conversion circuit 2 which converts a voltage supplied from a three-phase AC power source 1 into a DC voltage; the DC bypass capacitor 3 which accumulates the DC voltage; a high frequency square-wave inverter 4 which converts the DC voltage into a high frequency AC voltage; a high voltage transformer 5 which steps up an output voltage from the high frequency square-wave inverter to a high voltage; a rectifying circuit 6 which converts an output voltage from the high voltage transformer 5 into a DC voltage; an output smoothing capacitor 7 which accumulates an output voltage from the rectifying circuit 6; and a control circuit 19. If an exposure switch 18 is pressed, the control circuit 19 controls operations of the high frequency square-wave inverter 4 and the like so that the tube voltage and the tube current set in the input terminal 21 are applied between the cathode 82 and the anode 83 of the anode rotation type X-ray tube device 8. The anode rotation type X-ray tube device 8 to which the tube voltage and the tube current are supplied irradiates an object with X-rays.

The controller 23 performs control so that a rotation speed of the anode 83 reaches an irradiation possible rotation speed required to apply X-rays in an X-ray irradiation condition (a tube voltage, a tube current, a focal size, and the like) received by the input unit 21 at the time when the supply of the tube voltage and the tube current to the cathode 82 and the anode 83 of the anode rotation type X-ray tube device 8 is started. The controller 23 includes an X-ray irradiation condition reading unit 22, a calculation unit 234, the storage unit 230, a starter circuit driving trigger generation unit 24, an arrival time timer 233, and an X-ray exposure permission signal generation unit 25.

Figure 3:
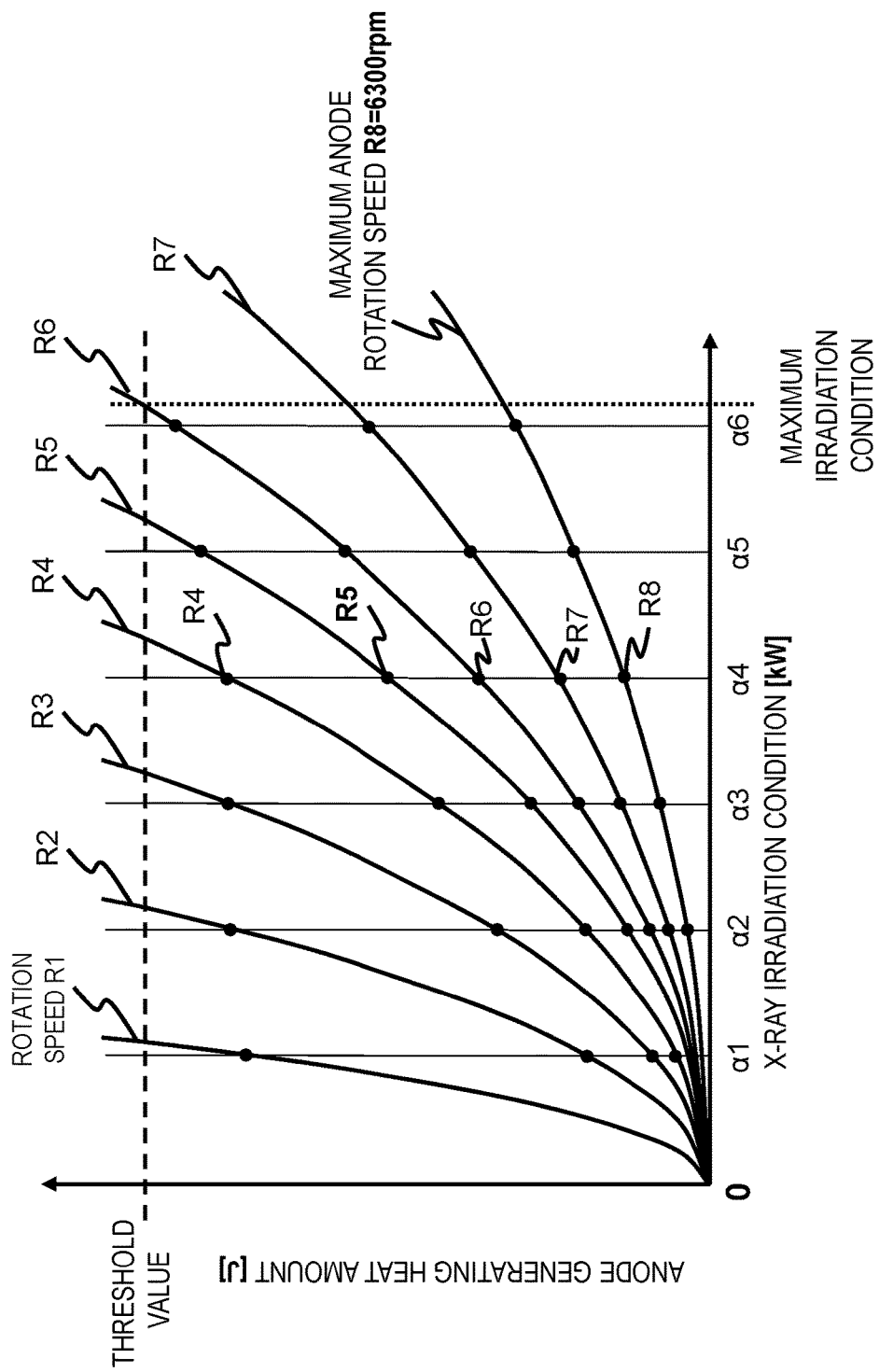
FIG. 3 is a graph illustrating a relationship between an X-ray irradiation condition and a heat unit generated in an anode in the X-ray tube device 8 of Embodiment 1 with respect to a plurality of rotation speeds.

The storage unit 230 is provided with the first storage section 231 which stores a relationship between X-ray irradiation conditions obtained in advance and irradiation possible rotation speeds as a table, and the second storage section 232 which stores irradiation possible rotation speeds obtained in advance and time (arrival time) required to reach the irradiation possible rotation speed as a table. A heat unit generated in the anode 83 differs depending on an X-ray irradiation condition (kW) (tube current×tube voltage) and a rotation speed of the anode 83 as illustrated in the graph of FIG. 3, and a heat unit generated in the anode 83 is reduced if a rotation speed of the anode 83 is increased. In addition, the anode 83 has an allowable heat unit threshold value. In the present embodiment, as illustrated in FIG. 3, anode rotation speeds (anode rotation speeds R4, R5, R6, R7, and R8 in FIG. 3) at which heat units generated in the anode 83 are lower than a threshold value in a certain X-ray irradiation condition α4 are obtained. Among the obtained anode rotation speeds, the lowest rotation speed R4 is referred to as an "irradiation possible rotation speed". The irradiation possible rotation speed is obtained for respective X-ray irradiation conditions (for example, α1 to α6). An obtained relationship between the X-ray irradiation condition and the irradiation possible rotation speed is stored in the first storage section 231, for example, in the form of a table.

Figure 4:
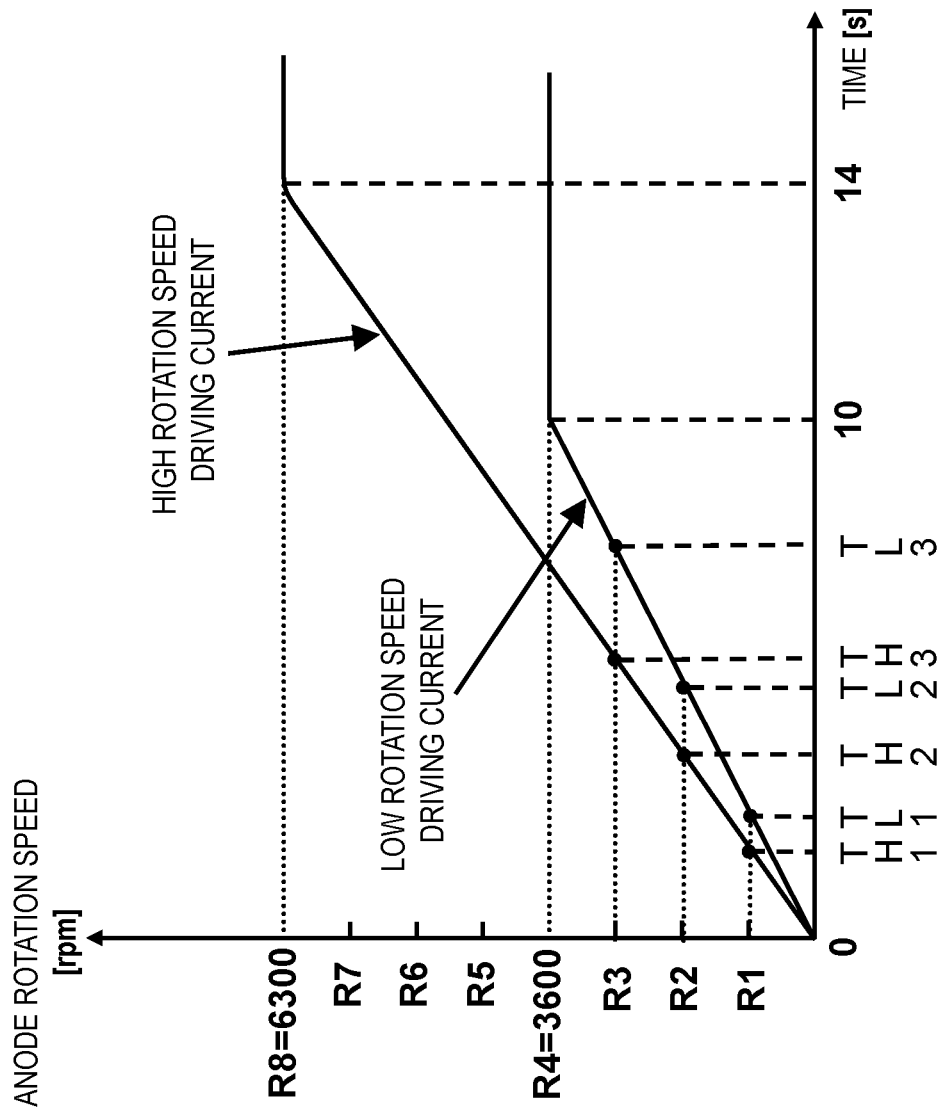
FIG. 4 is a graph illustrating a relationship between a time from starting the supply of a driving current to a stator coil 81 and an anode rotation speed in the rotary anode type X-ray tube device 8 of Embodiment 1.

On the other hand, a relationship between a time from starting the supply of a driving current to the stator coil 81 from the starter circuit 10 until a rotation speed reaches the rating rotation speed and the rotation speed is illustrated in a graph of FIG. 4. Therefore, a time (arrival time) to reach the irradiation possible rotation speed is obtained on the basis of the graph of FIG. 4 for each irradiation possible rotation speed stored in the first storage section 231, and is stored in the second storage section 232, for example, as a table.

As illustrated in FIG. 4, an increase in a rotation speed of the anode 83 differs depending on whether a driving current supplied to the stator coil 81 is used for a low rotation speed or a high rotation speed, and thus the arrival time is obtained depending on whether an X-ray irradiation condition corresponding to an irradiation possible rotation speed is a condition for supplying a low rotation speed driving current or a high rotation speed driving current. In addition, as will be described later, in a case where whether a low rotation speed driving current or a high rotation speed driving current is supplied is determined in a condition (for example, regarding only a tube current) which is different from an X-ray irradiation condition in which an irradiation possible rotation speed is obtained, two types of arrival times (TH1 to TH3 in a case of the high rotation speed driving current, and TL1 to TL3 in a case of the low rotation speed driving current) are obtained even at the same irradiation possible rotation speed, and are stored in the second storage section 232, and an arrival time is selected on the basis of a supplied driving current.

Hereinafter, an operation of each portion of the controller 23 will be described with reference to a flowchart illustrated in FIG. 5.

If an operator inputs object information or an X-ray irradiation condition (a tube current, a tube voltage, a focal size, and the like) from the input unit 21, and gives an instruction for starting X-ray irradiation preparation (steps S501 and S502), the X-ray irradiation condition reading unit 22 reads the input X-ray irradiation condition from the input terminal. The calculation unit 234 reads an irradiation possible rotation speed corresponding to the read X-ray irradiation condition (tube current×tube voltage) from the first storage section 231 which stores the relationship between an X-ray irradiation condition and an irradiation possible rotation speed (step S503).

In a case where the tube current of the X-ray irradiation condition is equal to or less than a predetermined value (for example, 300 mA), the calculation unit 234 determines that the low rotation speed driving current (a frequency of 60 Hz, a voltage of 180 Vrms, and a current of 14 Arms) should be supplied from the starter circuit 10 to the stator coil 81 in this condition, and proceeds to step S505. On the other hand, in a case where the tube current of the X-ray irradiation condition is more than the predetermined value (for example, 300 mA), the calculation unit 234 determines that the high rotation speed driving current (a frequency of 105 Hz, a voltage of 180 Vrms, and a current of 7 Arms) should be supplied from the starter circuit 10 to the stator coil 81 in this condition, and proceeds to step S506.

In steps S505 and S506, the calculation unit 234 obtains an arrival time corresponding to the irradiation possible rotation speed obtained in step S503 and the condition of the low rotation speed driving current or the high rotation speed driving current determined in step S504 on the basis of the relationship between an irradiation possible rotation speed and an arrival time stored in the second storage section 232.

The calculation unit 234 sets the obtained arrival time in the arrival time timer 233 (step S507). Successively, the calculation unit 234 controls the starter circuit driving trigger generation unit 24 to output a signal for giving an instruction for supplying the low rotation speed driving current or the high rotation speed driving current determined in step S504 and the starter circuit driving start signal to the starter circuit 10 (step S508). Consequently, the starter circuit 10 starts supplying the low rotation speed driving current (a frequency of 60 Hz, a voltage of 180 Vrms, and a current of 14 Arms) or the high rotation speed driving current (a frequency of 105 Hz, a voltage of 180 Vrms, and a current of 7 Arms) to the stator coil 81 in response to the instruction (step S509). The stator coil 81 supplied with the driving current generates an alternating magnetic field, and thus the anode 83 of the anode rotation type X-ray tube device 8 starts to be rotated. A rotation speed is increased with the passage of time as illustrated in the graph of FIG. 4.

The calculation unit 234 instructs the arrival time timer 233 to start counting (step S510). If the arrival time set in step S507 has elapsed (steps S511 and 512), it can be estimated that the rotation speed has reached the irradiation possible rotation speed obtained in step S503, and thus the X-ray exposure permission signal generation unit 25 outputs a signal for allowing the exposure switch 18 to be pushed (step S513) and also displays a state in which irradiation can be started on the display unit 26 (step S514). In addition, the display unit 26 displays information indicating irradiation waiting until the arrival time elapses.

If the operator pushes the exposure switch 18 in this state, the control circuit 19 of the high voltage generation unit 15 reads the X-ray irradiation condition (the tube voltage and the tube current) which is input to the input terminal 21, and supplies the tube voltage and the tube current to the cathode 82 and the anode 83 of the anode rotation type X-ray tube device 8 so that exposure to X-rays is performed (step S515).

As described above, in the present embodiment, a rating anode rotation speed is selected among a plurality of types thereof depending on an X-ray irradiation condition in the same manner as in the related art, and irradiation with X-rays is permitted if a rotation speed reaches an anode rotation speed (irradiation possible rotation speed) which is lower than the rating anode rotation speed and allows X-rays to be applied in the input X-ray irradiation condition. Consequently, irradiation with X-rays can be performed before reaching the rating anode rotation speed, and thus it is possible to reduce the operator's waiting time period. In addition, the anode rotation speed is continuously increased even after reaching the irradiation possible rotation speed as in the graph of FIG. 4, and then becomes constant at the rating rotation speed.

Further, in the present embodiment, whether or not to reach the irradiation possible rotation speed is determined on the basis of an elapsed time from starting rotation without detecting a rotation speed of the anode, and thus a waiting time period can be reduced with a simple configuration.

Still further, in the present embodiment, if a rating anode rotation speed is selected among a plurality of types thereof depending on an X-ray irradiation condition, and is within the range of the X-ray irradiation condition used for the selection, the rating anode rotation speed is not changed even if the X-ray irradiation condition is slightly changed. Therefore, an anode rotation speed may be controlled only by switching the types of driving currents supplied to the stator coil 81, and thus the control on the anode rotation speed can be easily performed.

In addition, in the present embodiment, a rating anode rotation speed has two types such as a low rotation speed and a high rotation speed, but three or more types thereof may be used.

Further, in the present embodiment, a relationship between an X-ray irradiation condition and the number of irradiation possible rotations is stored in the first storage section 231, and a relationship between an irradiation possible rotation speed and an arrival time is stored in the second storage section 232, but the two relationships may be combined as one relationship and thus a table or the like indicating a relationship between the X-ray irradiation condition and the arrival time may be stored in a single storage unit. In this case, step S503 illustrated in FIG. 5 may be omitted, and an arrival time may be directly obtained from an X-ray irradiation condition in steps S505 and S506.

Still further, in the present embodiment, the X-ray CT apparatus has been described, but the X-ray high-voltage device 13 of the present embodiment is also applicable to an X-ray scanning device.

(Embodiment 2)

Embodiment 2 will be described with reference to FIGS. 6 and 7.

Figure 6:
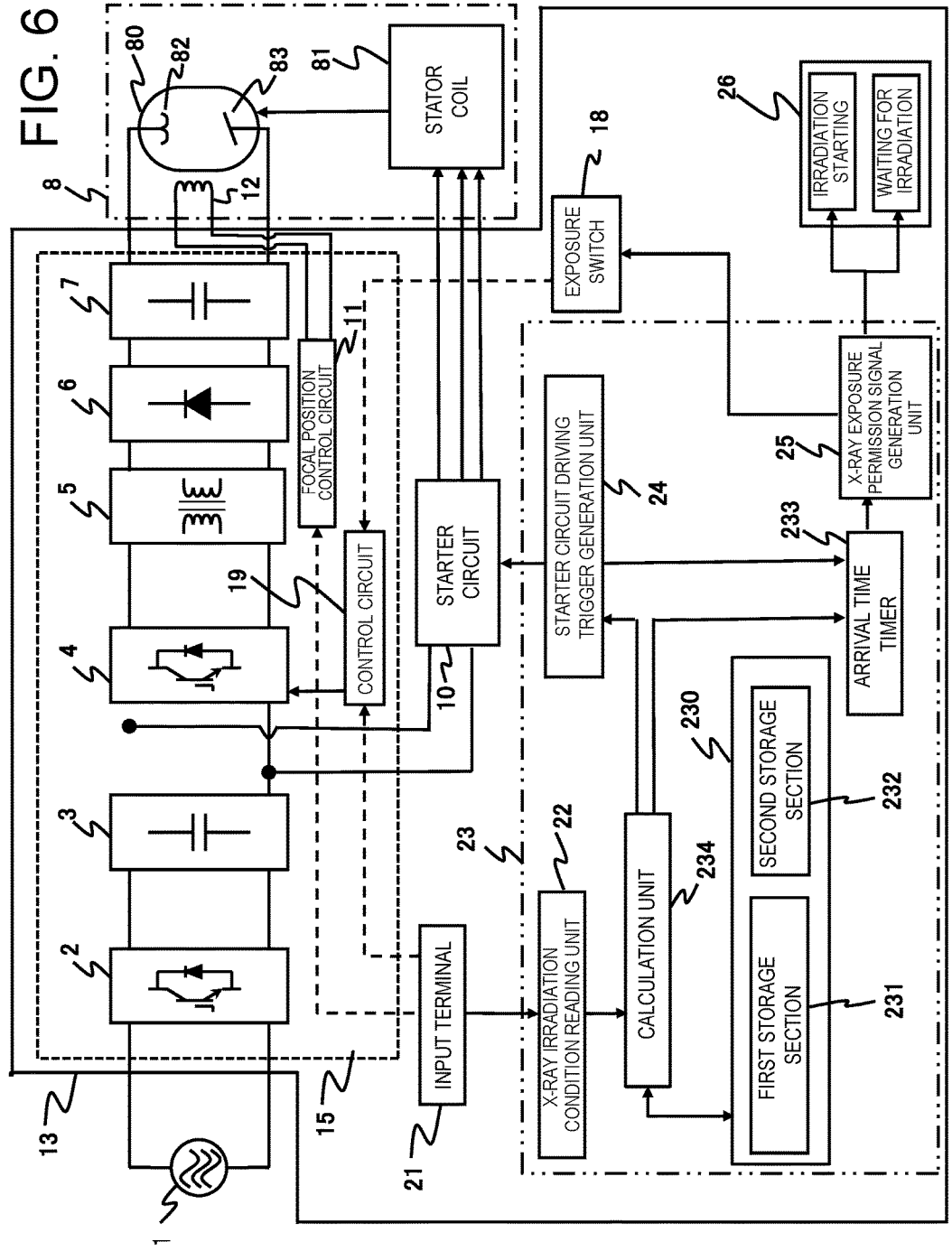
FIG. 6 is a block diagram illustrating a configuration of an X-ray high-voltage device 12 and a rotary anode type X-ray tube device 8 of an X-ray CT apparatus of Embodiment 2.

As illustrated in FIG. 6, an X-ray CT apparatus of Embodiment 2 includes a focal position control circuit 11 and a coil 12 which change a focal position on the anode 83 of an electron beam emitted from the cathode 82 of the rotary anode type X-ray tube device 8 in addition to the configuration of Embodiment 1. In the present embodiment, an X-ray irradiation condition received from an operator by the input terminal 21 includes an amplitude of a focal position in addition to a tube voltage, a tube current, and a focal size.

Generally, if a focal position of the anode rotation type X-ray tube device 8 is greatly changed, diffusion of a heat unit generated in the anode 83 increases, and if the focal position thereof is slightly changed, diffusion of the heat unit generated in the anode 83 decreases. For this reason, the larger the amplitude, the smaller the irradiation possible rotation speed, and thus an arrival time can be shortened. Therefore, in the present embodiment, a relationship between other X-ray irradiation conditions (a tube voltage, a tube current, and a focal size) and irradiation possible rotation speeds is obtained in advance for each amplitude of a focal position which can be set as an X-ray irradiation condition, and is stored in the first storage section 231 of the storage unit 230. The calculation unit 234 reads an irradiation possible rotation speed corresponding to X-ray irradiation conditions including the amplitude received by the input terminal 21 in step S503 of FIG. 5 from the first storage section 231. In steps S505 and S506, an arrival time corresponding to the read irradiation possible rotation speed is read from the second storage section 232.

Figure 7:
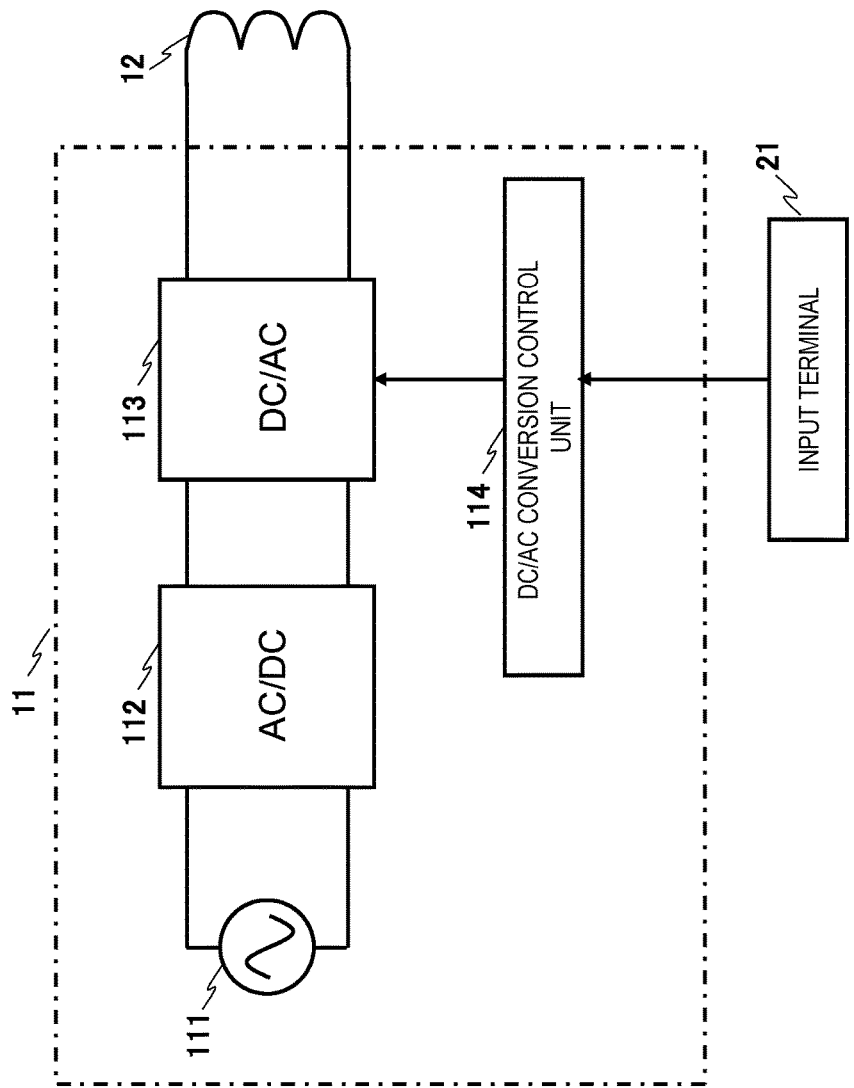
FIG. 7 is a block diagram illustrating a configuration of a focal position controller 11 of Embodiment 2.

As illustrated in FIG. 7, the focal position control circuit 11 includes an AC power source 111; an AC/DC conversion unit 112 which converts AC power output from the AC power source 111 into DC power; and a DC/AC conversion unit 113 which generates an AC signal having a current, a voltage, and a frequency corresponding to an output signal from a DC/AC conversion control unit 114 on the basis of an output from the AC/DC conversion unit 112. An AC signal generated by the DC/AC conversion unit 113 is supplied to the coil 12. The coil 12 generates a magnetic field for changing a focal position of an electron beam emitted from the cathode 82. The coil 12 and the DC/AC conversion control unit 114 read the amplitude of the focal position set in the input terminal 21, and an output from the DC/AC conversion control unit 114 is controlled so that the coil 12 generates a magnetic field for realizing the amplitude. In addition, a configuration for changing a focal position on the anode 83 may include an electrode generating a magnetic field, and a control circuit controlling a potential applied to the electrode.

Other configurations are the same as those in Embodiment 1, and thus description thereof will be omitted.

In Embodiment 2, in the X-ray CT apparatus including the focal position control circuit 11, an anode rotation speed is obtained by taking into consideration the amplitude of a focal position along with an X-ray irradiation condition, and thus it is possible to further reduce the operator's waiting time period until irradiation with X-rays is possible.

(Embodiment 3)

Figure 8:
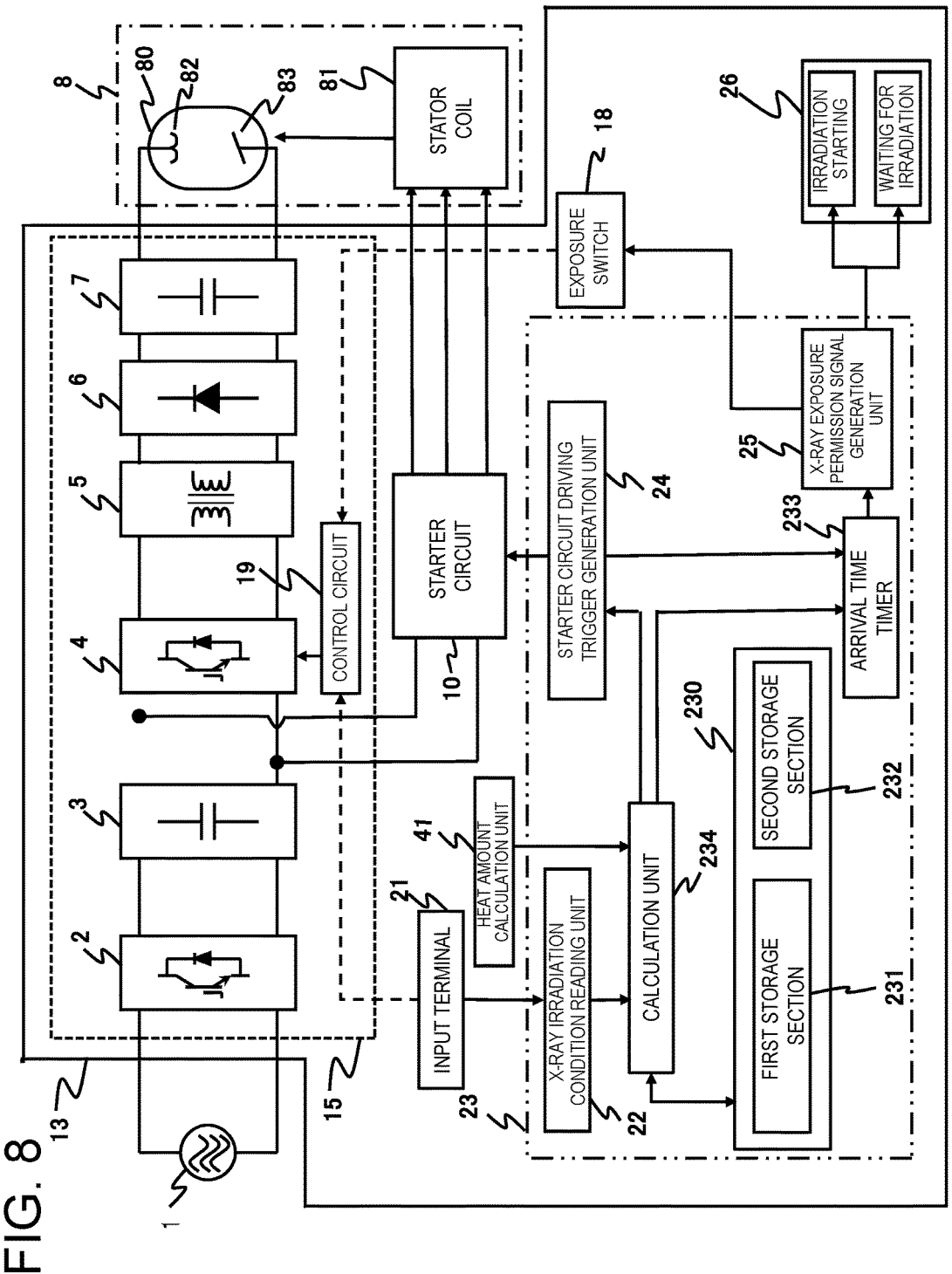
FIG. 8 is a block diagram illustrating a configuration of an X-ray high-voltage device 12 and a rotary anode type X-ray tube device 8 of an X-ray CT apparatus of Embodiment 3.
Figure 9:
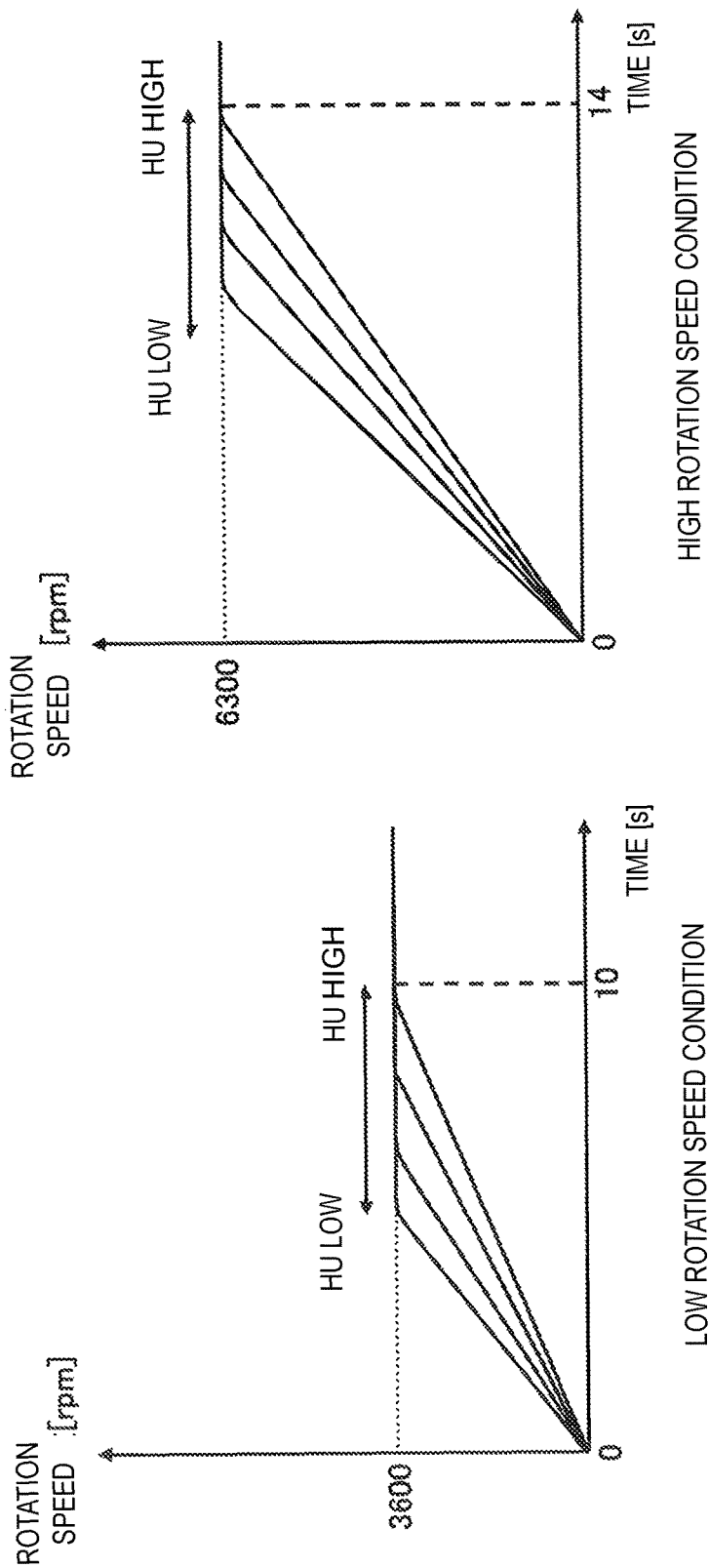
FIG. 9 is a graph illustrating a relationship between a time from starting the supply of a driving current to a stator coil 81 and an anode rotation speed in the rotary anode type X-ray tube device 8 of Embodiment 3 with respect to each heat unit (HU).

With reference to FIGS. 8 and 9, an X-ray CT apparatus of Embodiment 3 will be described.

As illustrated in FIG. 8, the X-ray CT apparatus of Embodiment 3 includes a heat unit (HU) calculation unit 41 which calculates a heat unit applied to the anode 83 of the rotary anode type X-ray tube device 8 and heat units accumulated in the anode 83 over an elapsed time period in addition to the configuration of Embodiment 1. As a heat unit calculation method in the heat unit calculation unit 41, a well-known calculation method is used in which heat dissipation or the like due to the passage of time is subtracted from heat units accumulated on the basis of history of electron beams with which the anode 83 is irradiated up to that time.

The temperature of the anode 83 of the rotary anode type X-ray tube device 8 is increased due to heat caused by irradiation with X-rays, and the anode is unlikely to be rotated at a high temperature more than at a normal temperature. For this reason, in a case where an arrival time of an irradiation possible rotation speed is to be obtained without taking into consideration the temperature of the anode 83, a relationship between an irradiation possible rotation speed and an arrival time is required to be set assuming that the temperature of the rotary anode type X-ray tube device 8 is highest. In Embodiment 3, an arrival time required for a rotation speed of the anode to reach an irradiation possible rotation speed is obtained from the second storage section 232 on the basis of a heat unit obtained by the heat unit calculation unit 41.

Specifically, a relationship between an irradiation possible rotation speed and an arrival time is stored in the second storage section 232 for each heat unit within an expectable range. For example, as illustrated in FIG. 9, graphs exhibiting a relationship between an elapsed time and an anode rotation speed for each heat unit (HU) are obtained for cases where a low rotation speed driving current is supplied and a high rotation speed driving current is supplied, and an arrival time to arrive an irradiation possible rotation speed is obtained for each heat unit (HU) and is stored in the second storage section 232 in the same manner as in Embodiment 1.

Figure 5:
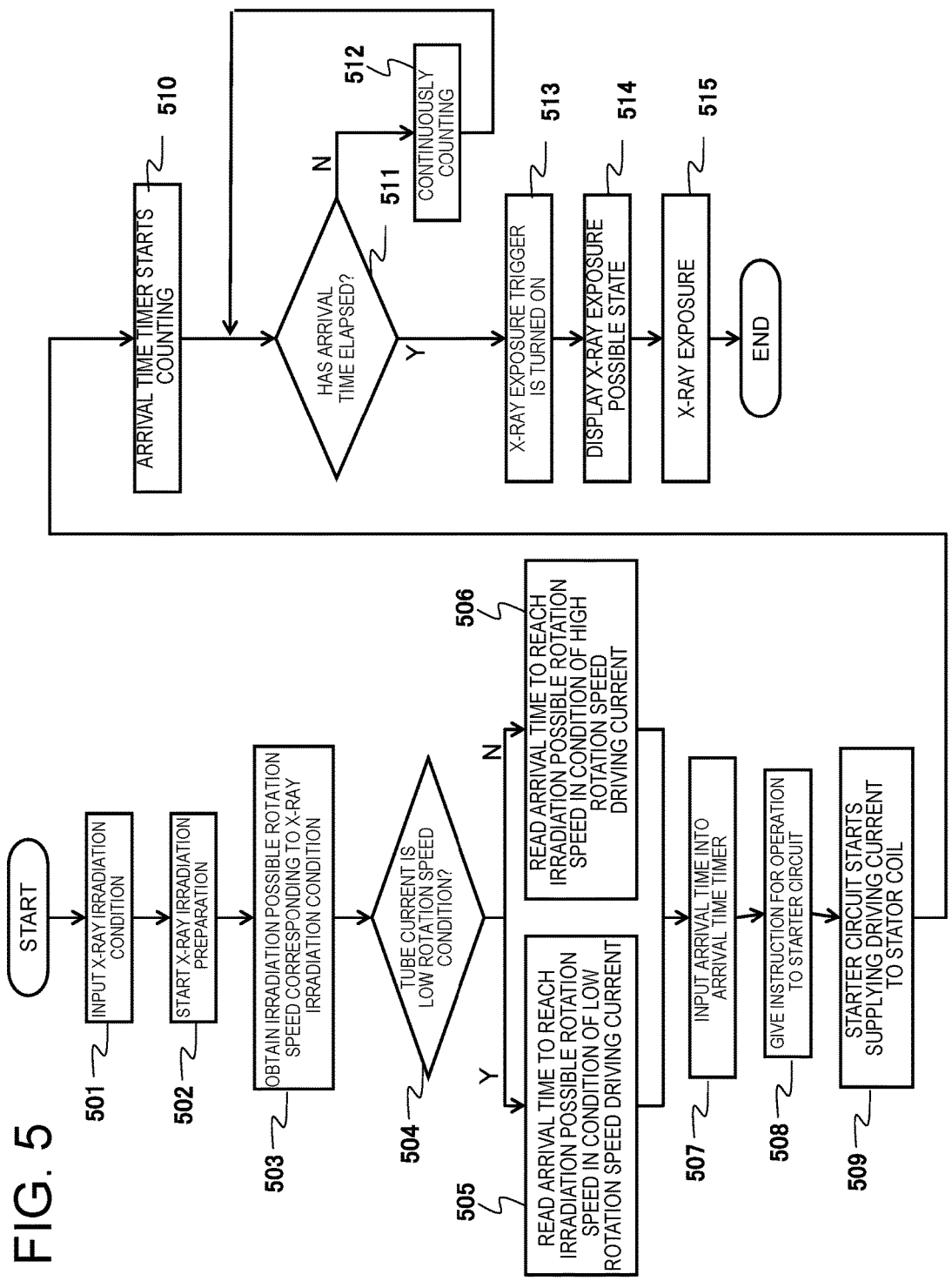
FIG. 5 is a flowchart illustrating operations of a controller 23 and the like of Embodiment 1.

The calculation unit 234 reads an irradiation possible rotation speed corresponding to an X-ray irradiation condition received by the input terminal 21 from the first storage section 231 in step S503 of FIG. 5 in the same manner as in Embodiment 1. In steps S505 and S506, an arrival time corresponding to the irradiation possible rotation speed read in step S503 is read from the second storage section 232 on the basis of a heat unit obtained by the heat unit calculation unit 41.

Other configurations and operations are the same as those in Embodiment 1, and description thereof will be omitted.

According to Embodiment 3, a waiting time period can be reduced until irradiation with X-rays is possible by taking into consideration a heat unit of the anode 83 during irradiation with X-rays.

In the above-described embodiments, the X-ray CT apparatus has been described, but the X-ray high-voltage device of the present embodiment is also applicable to an X-ray scanning device.

REFERENCE SIGNS LIST

1 THREE-PHASE AC POWER SOURCE, 2 AC-DC CONVERSION CIRCUIT, 3 DC BYPASS CAPACITOR, 4 HIGH FREQUENCY SQUARE-WAVE INVERTER, 5 HIGH VOLTAGE TRANSFORMER, 6 RECTIFYING CIRCUIT, OUTPUT SMOOTHING CAPACITOR, 8 ROTARY ANODE TYPE X-RAY TUBE, STARTER CIRCUIT, 11 FOCAL POSITION CONTROL CIRCUIT, 12 COIL, X-RAY HIGH-VOLTAGE DEVICE, 21 INPUT TERMINAL (INPUT UNIT), X-RAY IRRADIATION CONDITION READING UNIT, 23 CONTROLLER, STARTER CIRCUIT DRIVING TRIGGER GENERATION UNIT, 25 X-RAY EXPOSURE PERMISSION SIGNAL GENERATION UNIT, 26 DISPLAY UNIT, HEAT UNIT CALCULATION UNIT, 81 STATOR COIL, 101 STARTER CIRCUIT INVERTER, 102 STARTER CIRCUIT OUTPUT FILTER INDUCTOR, 103 OUTPUT FILTER CAPACITOR, 104 STARTER CIRCUIT INVERTER DRIVE CIRCUIT, 111 AC POWER SOURCE, 112 AC/DC CONVERSION UNIT, 113 DC/AC CONVERSION UNIT, 114 DC/AC CONVERSION CONTROL UNIT, 231 FIRST STORAGE SECTION, 232 SECOND STORAGE SECTION, 233 ARRIVAL TIME TIMER

The invention claimed is:

1. An X-ray CT apparatus comprising:
    an input unit that receives an X-ray irradiation condition for a mounted rotary anode type X-ray tube device;
    a starter circuit that supplies driving power for rotating an anode to the rotary anode type X-ray tube device; and
    a controller,
    wherein the controller selects one of predefined two or more types of rating anode rotation speeds depending on the X-ray irradiation condition received by the input unit, instructs the starter circuit to supply driving power for realizing the selected rating anode rotation speed, obtains an arrival time required for a rotation speed of the anode to reach an irradiation possible rotation speed which is lower than the rating anode rotation speed and is required to apply X-rays in the X-ray irradiation condition received by the input unit, and outputs information indicating that irradiation with X-rays is possible to a display unit after the arrival time has elapsed from starting the supply of the driving power by the starter circuit.

2. The X-ray CT apparatus according to claim 1, wherein the controller includes a storage unit that stores a relationship between various X-ray irradiation conditions and the arrival time and reads the arrival time corresponding to the X-ray irradiation condition received by the input unit from the storage unit.

3. The X-ray CT apparatus according to claim 1, wherein the controller obtains an irradiation possible rotation speed required to apply X-rays in the X-ray irradiation condition received by the input unit and obtains the arrival time on the basis of the irradiation possible rotation speed.

4. The X-ray CT apparatus according to claim 1, wherein the controller includes a first storage section that stores a relationship between various X-ray irradiation conditions and the irradiation possible rotation speed and a second storage section that stores a relationship between the irradiation possible rotation speed and the arrival time, reads the irradiation possible rotation speed corresponding to the X-ray irradiation condition received by the input unit from the first storage section, and reads the arrival time corresponding to the read irradiation possible rotation speed from the second storage section.

5. The X-ray CT apparatus according to claim 1, further including:
    a focal position controller that changes a focal position on the anode of an electron beam emitted from a cathode of the rotary anode type X-ray tube device, wherein the X-ray irradiation condition received by the input unit includes an amplitude of the focal position.

6. The X-ray CT apparatus according to claim 5, wherein the controller includes a first storage section that stores a relationship between other X-ray irradiation conditions excluding an amplitude of a focal position and the irradiation possible rotation speed for each amplitude of the focal position included in the X-ray irradiation conditions and a second storage section that stores a relationship between the irradiation possible rotation speed and the arrival time, reads the irradiation possible rotation speed corresponding to the X-ray irradiation conditions including the amplitude received by the input unit from the first storage section, and reads the arrival time corresponding to the read irradiation possible rotation speed from the second storage section.

7. The X-ray CT apparatus according to claim 1, further including:
a heat unit calculation unit that calculates a heat unit applied to the anode of the rotary anode type X-ray tube device, and heat units accumulated in the anode over an elapsed time period,
wherein the controller obtains the arrival time required for a rotation speed of the anode to reach the irradiation possible rotation speed on the basis of the heat unit obtained by the heat unit calculation unit.

8. The X-ray CT apparatus according to claim 7, wherein the controller includes a first storage section that stores a relationship between an X-ray irradiation condition and the irradiation possible rotation speed and a second storage section that stores a relationship between the irradiation possible rotation speed and the arrival time for each heat unit within a predetermined range, reads the irradiation possible rotation speed corresponding to the X-ray irradiation condition received by the input unit from the first storage section, and reads the arrival time corresponding to the read irradiation possible rotation speed from the second storage section on the basis of the heat unit obtained by the heat unit calculation unit.

9. The X-ray CT apparatus according to claim 1, further comprising:
a rotation portion that mounts the rotary anode type X-ray tube device thereon; and
a rotation driving portion that rotates the rotation portion around an object.

10. An X-ray high-voltage device comprising:
an input unit that receives an X-ray irradiation condition for a rotary anode type X-ray tube device;
a starter circuit that supplies driving power for rotating an anode to the rotary anode type X-ray tube device; and
a controller,
wherein the controller selects one of predefined two or more types of rating anode rotation speeds depending on the X-ray irradiation condition received by the input unit, instructs the starter circuit to supply driving power for realizing the selected rating anode rotation speed, obtains an arrival time required for a rotation speed of the anode to reach an irradiation possible rotation speed which is lower than the rating anode rotation speed and is required to apply X-rays in the X-ray irradiation condition received by the input unit, and outputs information indicating that irradiation with X-rays is possible to a display unit after the arrival time has elapsed from starting the supply of the driving power by the starter circuit.

11. An X-ray scanning device including:
an input unit that receives an X-ray irradiation condition for a mounted rotary anode type X-ray tube device;
a starter circuit that supplies driving power rotating an anode to the rotary anode type X-ray tube device; and
a controller,
wherein the controller selects one of predefined two or more types of rating anode rotation speeds depending on the X-ray irradiation condition received by the input unit, instructs the starter circuit to supply driving power for realizing the selected rating anode rotation speed, obtains an arrival time required for a rotation speed of the anode to reach an irradiation possible rotation speed which is lower than the rating anode rotation speed and is required to apply X-rays in the X-ray irradiation condition received by the input unit, and outputs information indicating that irradiation with X-rays is possible to a display unit after the arrival time has elapsed from starting the supply of the driving power by the starter circuit.

* * * * *